United States Patent
Drummond, III

(10) Patent No.: US 9,364,512 B1
(45) Date of Patent: Jun. 14, 2016

(54) ALOE VERA BASED VAPING COMPOSITIONS

(71) Applicant: Halister Joseph Drummond, III, Austin, TX (US)

(72) Inventor: Halister Joseph Drummond, III, Austin, TX (US)

(73) Assignee: Halister Joseph Drummond, III, Austin, TX (US)

( * ) Notice: Subject to any disclaimer, the term of this patent is extended or adjusted under 35 U.S.C. 154(b) by 0 days.

(21) Appl. No.: 14/616,717

(22) Filed: Feb. 8, 2015

(51) Int. Cl.
| | |
|---|---|
| *A61K 9/12* | (2006.01) |
| *A61K 36/886* | (2006.01) |
| *A61K 9/00* | (2006.01) |
| *A61K 31/4045* | (2006.01) |
| *A61K 33/30* | (2006.01) |
| *A61K 38/06* | (2006.01) |
| *A61K 31/714* | (2006.01) |
| *A61K 31/519* | (2006.01) |
| *A61K 31/047* | (2006.01) |
| *A61K 31/198* | (2006.01) |
| *A61K 31/05* | (2006.01) |

(52) U.S. Cl.
CPC .............. *A61K 36/886* (2013.01); *A61K 9/007* (2013.01); *A61K 9/0043* (2013.01); *A61K 31/047* (2013.01); *A61K 31/05* (2013.01); *A61K 31/198* (2013.01); *A61K 31/4045* (2013.01); *A61K 31/519* (2013.01); *A61K 31/714* (2013.01); *A61K 33/30* (2013.01); *A61K 38/063* (2013.01)

(58) Field of Classification Search
CPC ........................... A61K 9/0043; A61K 36/886
See application file for complete search history.

(56) References Cited

PUBLICATIONS http: aloecadrabra.com ingredients, Living well Brands, 2015.*
http://azarius.net/encyclopedia/77/Best_temperatures_for_vaporizing_herbs, 2015.*
http://blog.listentoyourgut.com/inhaled-glutathione-for-lung-inflammation-pneumonia-emphysema, 2015.*
http://www.researchgate.net/publication/48347118_aloe_vera_their_chemicals_composition_and applications_A_review, 2015.*
https://www.reddit.com/r/DIY_eJuice/comments/3ya1un/is_there_something_that_would_stop_oxidation_in/, 2016.*

* cited by examiner

*Primary Examiner* — Carlos Azpuru

(57) ABSTRACT

An aloe vera based liquid composition comprising at least one antioxidant agent that reduces oxidative stress in the lungs and delivers various antioxidants and nutrients when absorbed upon vaping by the user.

9 Claims, No Drawings

ALOE VERA BASED VAPING COMPOSITIONS

TECHNICAL FIELD OF THE INVENTION

The invention relates to vaping compositions for inhalation that decrease oxidative stress and enhance nutrient uptake. More particularly a nicotine-free antioxidant vaping solution intended to be atomized or vaporized and inhaled for absorption with effect of supporting the body's ability to decrease local inflammation by decreasing oxidative stress caused by free radicals and reactive oxygen species (ROS) and improving the nutrient status of the vaping individual.

BACKGROUND OF THE INVENTION

A number of lung diseases and irritations are associated with free radicals. A free radical is a molecular species having a single unpaired electron available in an outer orbital. Free radicals can initiate chain reactions in cells and body fluids that damage organic molecules, including biomolecules (e.g., DNA, lipids, and proteins). Free radicals are formed endogenously (e.g., by cellular metabolism, inflammation by immune cells, and the like) and exogenously (e.g., by radiation, pharmaceuticals, hydrogen peroxide, toxic chemicals, smoke, alcohol, oxidized polyunsaturated fats, and the like). For example, a person may inhale a superoxide radical. Once generated, the superoxide radical may degenerate into other free radicals such as hydrogen peroxide and hydroxide radicals.

The damage caused by free radicals often is referred to as "oxidative stress." ROS are free radical generators with cytotoxic consequences of a mismatch between the production of free radicals and the ability of a cell to defend against them. Oxidative stress may be caused by a combination of the following: increase in the formation of free radicals, an decrease in scavenging of free radicals, or decreased repair of free-radical-modified macromolecules.

The pulmonary system is particularly vulnerable to ROS-induced injury because of its continuous exposure to toxic pollutants from a wide variety of sources in the ambient air: asbestos, crystalline silica, coal, chromium, herbicides, cigarette smoke, and smog. Oxidative stress causes inflammation, a complex phenomenon that is associated with a variety of respiratory disorders such as allergies, asthma, lung cancer, and COPD. These disorders may induce a feeling of dryness, burning, and persistent irritation in the respiratory tract. In severe cases it can produce pain, hypoxia, scarring, interstitial lung disease, and opportunistic infection. Respiratory diseases threaten the health of many people, and their treatment often is costly. Respiratory irritations are also problematic, among other things, because they cause great discomfort and can lead to secondary opportunistic problems, such as infection. Methods and compositions are needed for providing antioxidants in efficacious amounts to the lungs.

Certain molecules, termed antioxidants, are capable of scavenging free radicals and subsequently protecting cells from damage due to oxidative stress. Antioxidants protect cells from free radicals by inhibiting free radical formation, intercepting free radicals, and repairing free-radical-induced injury. However, delivery of antioxidants to the lungs is difficult. When administered orally, antioxidants may have, among other things, poor lung penetration, a high dosage requirement, and lower bioavailability.

The present inventor has found that respiratory compositions comprising aloe vera in combination with amino acids and other nutrients when vaped provides for a decrease in oxidative stress that may be contributing to the process of inflammation.

Accordingly, an aspect of the present invention is to provide aloe vera liquid based vaping compositions for inhalation. Another aspect of the present invention is to provide aloe vera liquid based respiratory compositions that when vaped may reduce oxidative stress which may prevent, reduce, or alleviate inflammation. A further aspect of the present invention is to provide aloe vera based vaping compositions for inhalation comprising antioxidants like resveratrol, amino acids like gamma-aminobutyric acid, melatonin, and other molecules that may absorb locally when vaped and improve the nutrition status of the user.

SUMMARY

The objects, features and advantages of the present invention are to provide an aloe vera based vaping solution for atomizers and vaporizers that avoids the negative consequences of nicotine while providing the user with additional health benefits that can result from the infusion and absorption of vitamins by a user.

Aloe Vera liquid has proved effective in the treatment on internal and external wounds because of its following properties: anti-inflammatory, analgesic, aids in cellular penetration of source compounds, regenerates epithelium, increases immunity and is nontoxic. The above mentioned properties of aloe vera liquid are very valuable in the respiratory system. Current available nutrient liquids for vaping or inhaling do not incorporate aloe vera.

The investigation into the use of aloe vera in respiratory disorders was aimed at examining whether the anti-inflammatory and rapid tissue repairing properties of aloe vera, which have been successfully demonstrated in the treatment of internal and external wounds, could be applied to disorders of the lungs involving oxidative stress, inflammation, genetic conditions, and infection.

In certain embodiments, the present invention provides compositions comprising at least one antioxidant agent chosen from a carotenoid, glutathione (multiple forms and enhancers), alpha lipoic acid, a flavonoid, an amino acid, aloe vera liquid, n-acetyl cysteine, an omega-6 fatty acid, melatonin, and vitamin E acetate. The compositions of the present invention also may comprise a lubricating agent, as well as other components of therapeutic benefit or useful to form a composition for delivery to the lungs.

The compositions of the present invention have antioxidant activity. The term "antioxidant activity" refers to an inhibitory effect on biological oxidative processes involving free radicals or ROS. In addition to antioxidant activity, certain embodiments of the compositions of the present invention also may have activity as one or more of a lubricant, a nitric oxide synthase inhibitor, an anti-inflammatory, a neuroprotectant, a bacteriocidal, and a bacteriostatic.

The compositions of the present invention may be in a variety of forms, such as the form of a solution, a suspension, an emulsion, a spray, or the like. The viscosity of the compositions may be increased to increase retention time in the lungs, reduce drainage rates, or increase bioavailability. The compositions of the present invention offer a significant advantage over oral administration of antioxidant agents, among other things, by overcoming the difficulty of poor gastrointestinal absorption, by using a lower dosage than would be required by oral administration, and by allowing more of the active agents to provide antioxidant action.

The features and advantages of the present invention will be readily apparent to those skilled in the art upon a reading of the description of the embodiments that follows.

DETAILED DESCRIPTION

The compositions, of the present invention can comprise, consist essentially of, or consist of, the essential as well as optional ingredients and components described herein. As used herein, "consisting essentially of" means that the composition or component may include additional ingredients, but only if the additional ingredients do not materially alter the basic and novel characteristics of the claimed compositions or methods.

All publications cited herein are hereby incorporated by reference in their entirety. As used herein, a "nutritionally acceptable" component is one that is suitable for use with humans and/or animals without undue adverse side effect's (such as toxicity, irritation, and allergic response) commensurate with a reasonable benefit/risk ratio and are considered USP or pharmaceutical grade nutritional supplements.

By "safe and effective amount" is meant an amount of a compound or composition which is high enough to address oxidative stress by quenching free radicals and ROS, but low enough to avoid serious side effects at a reasonable benefit/risk ratio within the scope of sound judgement. The safe and effective amount may vary with the age and physical condition of the person being treated, the severity of the condition, the specific ingredients employed, and like factors.

This invention relates to compositions useful in reduction of oxidative stress in the lungs. The compositions of the present invention may be used to support the body's ability to decrease inflammation caused by oxidative stress that is involved with, among other things, one or more of irritations of the lung, dryness of the lungs, and the onset or progression of a lung disease. The present invention provides compositions that may be used to promote lung health. As referred to herein, the term "lung diseases" will be understood to mean lung disorders including, but not limited to, acute bronchitis, cystic fibrosis, lung cancer, pneumonia, silicosis, chronic obstructive pulmonary disease, pneumoconiosis, pulmonary arterial hypertension, asthma, mesothelioma, sarcoidosis, and pneumonitis.

The concentration of the antioxidant agents in the compositions of the present invention may vary depending on a variety of factors, such as, for example, type of antioxidant agent used, bioavailability, potency, and the like. In general, the antioxidant agents should be present in the compositions of the present invention in the range of from about 0.001% to about 35% by weight of the composition, and may be suspended or dissolved. Antioxidant agents are available commercially from a variety of suppliers, including distributors, such as PCCA, Houston, Tex. and Medisca in Plattsburgh, N.Y. and Irving, Tex. and Las Vegas, Nev., as well as manufacturers, such as Technical Sourcing International, Inc., Missoula, Mont.

The percentage of the active ingredient in the foregoing compositions can be varied within wide limits, but for practical purposes it is preferably present in a concentration of at least 2% in a primary liquid composition. The most satisfactory compositions are those in which a much higher proportion of the active ingredient is present, for example, from 10% to 90% by weight.

One example of antioxidant agents suitable for use in the compositions of the present invention includes, among other things, aloe vera liquid. Aloe vera liquid is the substance produced by the parenchymal cells of the aloe vera plant, which is known to have antioxidant, anti-inflammatory, antibacterial, and antiviral properties. Aloe vera liquid is a complex mixture of components that includes, among other things, mono- and polysaccharides (e.g., acemannan), glycoproteins (e.g., alprogen, C-glucosyl chromone), lignan, salicylic acid, saponins, sterols, triterpenoids, glutathione peroxidase, superoxide dismutase isozymes, as well as vitamins and minerals. Aloe vera liquid also may induce expression of the antioxidant protein, metallothionein, as well as scavenge hydroxyl radicals and prevent suppression of superoxide dismutase and glutathione peroxidase. In certain embodiments, aloe vera liquid or aloe vera extract (freeze-dried powder) may be present in the compositions of the present invention in an amount in the range of from about 0.05% to about 90% by weight of the composition.

Preparation of the aloe vera liquid vaping solution was done through the hand filleting method. The aloe vera (*Aloe barbadensis*) leaves were processed as quickly as possible after cutting from the plant. The whole extraction process takes no more than 2 hrs. The leaf removed from the plant was exposed to ultraviolet light for disinfection then rinsed with sterilized water and dried. Then the inner leaf portion is separated from the leaf peeling away the cortex of the leaf. Homogenization was performed using a high-speed blender. The preparation was then fractionated. For the preparation of the final Aloe Vera liquid homogenate was towed, clarified, centrifuged at 10,000 rpm in a continues flow centrifuge and filtered through a 0.2µ pore filtration system. The final Aloe Vera liquid was sterile, aloin free, pulp free and mucilage free. The specific activity controls were done according to the International Aloe Science Council (IASC) recommendations.

Another example of an antioxidant agent suitable for use in the compositions of the present invention includes, among other things, carotenoids. In certain embodiments, carotenoids may be present in the compositions of the present invention in an amount in the range of from about 0.05% to about 2% by weight of the composition. Examples of suitable carotenoids include, but are not limited to, lutein and zeaxanthin. Zeaxanthin blocks the activity of peroxide radicals, inhibits low-density lipoprotein (LDL) oxidation, and protects cell membranes from free radical damage. Sulforaphane is another example of carotenoid suitable for use as an antioxidant agent in the compositions of the present invention. Sulforaphane can convert to glucosinolates in the human body, which may induce production of antioxidant-detoxifying enzymes such as glutatione-5-transferase and UDP-glucuronosyl transferase. Examples of other carotenoids that may be used as antioxidant agents in the compositions of the present invention include, but are not limited to, astaxanthin (ene), α and β-carotene, cantaxanthin, luteulin, lycopene, phystoene, fucoxanthan, periodinin, and xanthophylls.

Other examples of antioxidant agents suitable for use in the compositions of the present invention include, among other things, glutathione, reduced glutathione, and glutathione enhancers. Glutathione, reduced glutathione, and glutathione enhancers each may be present in the compositions of the present invention in an amount in the range of from about 0.05% to about 2% by weight of the composition. When reduced, glutathione scavenges, or neutralizes, a free radical to a less toxic or nontoxic molecule; glutathione then becomes "oxidized," most often to the glutathione disulfide anion radical. Examples of suitable glutathione enhancers include, among other things, L-cysteine, pyridoxine, and riboflavin. Other examples of suitable glutathione enhancers include, among other things, glutathione precursors, such as n-acetyl-cysteine.

Other examples of antioxidant agents suitable for use in the compositions of the present invention include, among other things, lipoic acids (e.g., α-lipoic acid, dihydrolipoic acid, and isolipoic acid). Besides lipoic acid's ability to inhibit free radicals, it is involved with regenerating other antioxidants that may protect the lungs. Treatment with lipoic acid also may enhance the activities of other antioxidant scavenging enzymes such as glutathione peroxidase, catalase, and ascorbate free radical reductase. In addition to having antioxidant properties, lipoic acid has anti-inflammatory and analgesic properties. Lipoic acids may be present in the compositions of the present invention in an amount in the range of from about 0.05% to about 2% by weight of the composition.

Other examples of antioxidant agents suitable for use in the compositions of the present invention include, among other things, flavonoids. Flavonoids are compounds that are present in a variety of plants and include phenolic compounds (e.g., proanthocyanins, anthocyanins, flavanoids, flavones, flavanones, flavonols, flavans, isoflavones, catechins, epicatechins, resveratrol, and phenolic acids) and monoterpenes (e.g., limonene). Flavonoids readily scavenge superoxide and hydroxyl free radicals and can inhibit lipid peroxidation, which may occur when the lungs are exposed to free radicals. In certain embodiments, flavonoids may be present in the compositions of the present invention in an amount in the range of from about 0.05% to about 2% by weight of the composition. Examples of suitable flavonoids include, but are not limited to, proanthocyanins. Proanthocyanins are phenolic polymers built from catechin or epicatechin monomer units and include, for example, catechin, epicatechin, catechin gallate, epicatechin gallate, gallocatechin gallate, and epigallocatechin gallate. Generally, the proanthocyanins are from two to seven catechin units long. Longer oligomers, and the monomeric catechin and epicatechin units, also have oxygen-scavenging capability. Proanthocyanins are found naturally in a variety of botanicals, such as grape seeds, pine bark, blackjack oak, horse chestnut, witch hazel, and hawthorn. Proanthocyanins are further found in apples, berries, barley, bean hulls, chocolate, rhubarb, rose hips, and sorghum. Synthetic analogs of the botanical extracts also exist and one skilled in the art, with the benefit of this disclosure, will recognize that such synthetic analogs may also be utilized in the present invention. In addition to having antioxidant properties, proanthocyanins also may be a neuronal cell protectant against cytotoxicity, and have the ability to regenerate the ascorbyl radical and protect endogenous vitamin E and glutathione from oxidative stress. Another example of a suitable flavonoid is resveratrol (3,4',5-trihydroxystilbene). Resveratrol and its glucoside, cis- and trans-forms occur naturally in a number of plant families including Vitaceae. These resveratrols possess many biological activities including antioxidant activity and anti-inflammatory properties. Other examples of suitable flavonoids include, but are not limited to, quercetin, rutin, genistein, citrus bioflavonoids (e.g., narigingin and flavone glycosides such as hesperidin), ellagic acid, and hydroxytyrosol.

Other examples of antioxidant agents suitable for use in the compositions of the present invention include, among other things, oleanoic acids. Oleanoic acids are antioxidants commonly found in plants. Oleanoic acids are capable of inhibiting free radicals. In certain embodiments, oleanoic acids may be present in the compositions of the present invention in an amount in the range of from about 0.05% to about 2% by weight of the composition.

Another example of an antioxidant agent suitable for use in the compositions of the present invention includes, among other things, ascorbyl palmitate. Ascorbyl palmitate is a synthetic ester of vitamin C that is fat-soluble, has a neutral pH, and is stable. Ascorbyl palmitate also may have anti-inflammatory activity within a cell, such as a cell in an alveolar sac. In certain embodiments, ascorbyl palmitate may be present in the compositions of the present invention in an amount in the range of from about 0.05% to about 2% by weight of the composition.

Other antioxidant agents suitable for use in the compositions of the present invention include, among other things, omega-6 fatty acids (e.g., γ-linolenic acid (GLA) and linoleic acid (LA)) and omega-3 fatty acids (e.g., eicosopentaenoic acid (EPA) and docosahexaenoic acid (DHA)). In certain embodiments, these fatty acids may be present in the compositions of the present invention, alone or in combination, in an amount in the range of from about 0.05% to about 2% by weight of the composition.

Other antioxidant agents suitable for use in the compositions of the present invention include, among other things, melatonin and vitamin E acetate. In certain embodiments, melatonin may be used in the compositions of the present invention in an amount in the range of from about 0.05% to about 2% by weight of the composition. In other embodiments, vitamin E acetate may be used in the compositions of the present invention in an amount in the range of from about 0.05% to about 1.5% by weight of the composition.

In certain embodiments, two or more antioxidant agents may be chosen and combined so as to have a synergistic antioxidant activity. Synergy of antioxidant agent combinations may be measured using an antioxidant activity assay known in the art, for example, the Total Oxyradical Scavenging Capacity (TOSC) Assay.

Finally, so-called "natural" anti-inflammatory agents are useful in methods of the subject invention. Such agents may suitably be obtained as an extract by suitable physical and/or chemical isolation from natural sources (e.g., plants, fungi, by-products of microorganisms). For example, candelilla wax, alpha bisabolol, aloe vera, Manjistha (extracted from plants in the genus *Rubia*, particularly *Rubia Cordifolia*), and Guggal (extracted from plants in the genus *Commiphora*, particularly *Commiphora Mukul*), kola extract, chamomile, and sea whip extract, may be used.

Additional anti-inflammatory agents useful herein include compounds of the Licorice (the plant genus/species *Glycyrrhiza glabra*) family, including glycyrrhetic acid, glycyrrhizic acid, and derivatives thereof (e.g., salts and esters). Suitable salts of the foregoing compounds include metal and ammonium salts. Suitable esters include $C_2$-$C_{24}$ saturated or unsaturated esters of the acids, preferably $Cio$-$C_{24}$, more preferably $C_{16}$-$C_{24}$. Specific examples of the foregoing include oil soluble licorice extract, the glycyrrhizic and glycyrrhetic acids themselves, monoammonium glycyrrhizinate, monopotassium glycyrrhizinate, dipotassium glycyrrhizinate, 1-beta-glycyrrhetic acid, stearyl glycyrrhetinate, and 3-stearyloxy-glycyrrhetinic acid, and disodium 3-succinyloxy-beta-glycyrrhetinate. Stearyl glycyrrhetinate is preferred.

Mixtures of any of the above anti-inflammatory agents can also be used.

The compositions of the present invention also may comprise other components useful to form a vaping preparation. Such components include a vehicle (e.g., water), buffers, organic carriers, inorganic carriers, emulsifiers, wetting agents, and the like. In certain embodiments, the compositions of the present invention also may comprise other components, including anti-inflammatory agents, penetration enhancers (e.g., methyl-sulfonyl-methane), propylene glycol, nitric oxide synthase inhibitors (e.g., L-arginine), hyaluronic acid, and collagen.

Examples of vehicles include water, water mixtures of lower alkanols, vegetable oils, polyalkylene glycols, petroleum-based jelly, ethylcellulose, ethyl oleate, carboxymethylcellulose, polyvinylpyrrolidone, and isopropyl myristate.

In general, the compositions of the present invention should have an osmotic pressure sufficient to approximate the osmotic pressure of the fluids naturally found in the lungs. If necessary, the osmotic pressure can be adjusted by using appropriate amounts of physiologically acceptable salts or excipients. For example, sodium chloride may be added to the compositions of the present invention to approximate fluids naturally found in the lungs. When included, sodium chloride typically is used in amounts ranging from about 0.01% to about 1% by weight of the composition. Equivalent amounts of one or more salts made up of cations (e.g., potassium and ammonium) and anions (e.g., chloride, citrate, ascorbate, borate, phosphate, bicarbonate, sulfate, thiosulfate, bisulfate, sodium bisulfate, and ammonium sulfate) may also be used in addition to or instead of sodium chloride to achieve osmolarities within the above-stated range. Sugars like mannitol, dextrose, glucose, or other polyols also may be added to adjust osmolarity.

The compositions of the present invention also may comprise a buffering agent to, among other things, control pH and to prevent pH drift under storage conditions. Any pharmaceutically acceptable buffering agent may be utilized. Suitable buffering agents are known in the art and may include one or more of zinc sulfate, boric acid, sodium borate, potassium (e.g., potassium bicarbonate), sodium phosphate, sodium acetate, and sodium citrate. When present, the particular concentration will vary, depending on the agent employed. In general, however, the buffering agent should be used in an amount sufficient to maintain a target pH in the range of from about 6.0 to about 8.0. An additional benefit of including zinc sulfate as a buffering agent is its role as a cofactor for antioxidant scavenging enzymes.

The compositions of the present invention also may include a preservative. Any known preservative suitable for inhalation may be used. For example, the preservative may be benzalkonium chloride and other quaternary ammonium preservative agents, sorbic acid, disodium edetate, ethylenediaminetetraacetic acid (EDTA), and methyl- and propylparaben. When present, the amount of preservative used may depend on the particular preservative chosen. In certain embodiments, the preservative may be present in the compositions of the present invention in an amount of from about 0.001% to about 1% by weight of the composition. In certain embodiments, the optional preservative should be chosen to minimize any reduction in the storage stability of the components present in the composition, or to minimize any adverse interactions with these components, or both. Examples of such a preservative are the systems disclosed in U.S. Pat. Nos. 5,576,028 and 5,607,698, the relevant disclosures of which are incorporated herein by reference. These systems use a low amount of hydrogen peroxide, or a peroxide source, as a preservative in combination with a peroxy stabilizer, such as a phosphonic acid (e.g., diethylene triamine penta(methylene-phosphonic acid).

One example of a formulation of a composition of the present invention is a composition comprising the components in Table 1.

TABLE 1

| Component | Amount (%) |
|---|---|
| Aloe Vera | 40 q.s. |
| glycerin* | 60 |
| Gamma aminobutyric acid | 10 |
| Melatonin | 2 |
| Zinc sulfate heptahydrate | 0.5 |
| Benzalkonium chloride | 0.01 |

*May include other components such as, for example, sodium citrate, sodium chloried, citric acid, and water.

Another example of a formulation of a composition of the present invention is a composition comprising the components in Table 2.

TABLE 2

| Component | Amount (%) |
|---|---|
| Aloe Vera | 50 q.s. |
| glycerin* | 50 |
| n-acetyl-cysteine | 10 |
| Melatonin | 2 |
| Glutathione | 10 |

*May include other components such as, for example, boric acid, potassium chloride, sodium chloride, sodium borate, sodium hydroxide (to adjust pH), and water.

Another example of a formulation of a composition of the present invention is a composition comprising the components in Table 3.

TABLE 3

| Component | Amount (%) |
|---|---|
| Aloe Vera | 30 q.s. |
| glycerin* | 70 |
| Methylcobalamin | 0.1 |
| Methyltetrahydrofolate | 0.1 |
| Zeaxanthin | 0.2 |

*May include other components such as, for example, boric acid, calcium chloride, sodium perborate, phosphoric acid, potassium chloride, hydroxypropyl methylcellulose, and water.

Another example of a formulation of a composition of the present invention is a composition comprising the components in Table 4.

TABLE 4

| Component | Amount (%) |
|---|---|
| Aloe Vera | 70 q.s. |
| glycerin* | 30 |
| Theanine | 5 |
| Resveratrol | 5 |

*May include other components such as, for example, boric acid, propylene glycol, calcium chloride, sodium perborate, phosphoric acid, potassium chloride, benzalkonium chloride, and water.

Therefore, the present invention is well adapted to carry out the objects and attain the ends and advantages mentioned as well as those that are inherent therein. While numerous changes may be made by those skilled in the art, such changes are encompassed within the spirit of this invention as defined by the appended claims.

This invention relates to compositions useful as vaped antioxidants. The compositions of the present invention may be helpful in decreasing oxidative stress. Oxidative stress has been shown to play a role in the process of inflammation in the lungs. Methods of decreasing inflammation and nutrient absorption using the above compositions are also disclosed.

All percentages and ratios used herein are by weight of the total composition and all measurements are at 25 C, unless otherwise designated.

The compositions in the following illustrate specific embodiments of the gastrointestinal compositions of the present invention, but are not intended to be limiting thereof. Other modifications can be undertaken by the skilled artisan without departing from the spirit and scope of this invention.

All exemplified compositions can be prepared by conventional formulation and mixing techniques. Component amounts are listed as weight percents and exclude minor materials such as diluents, filler, and so forth. The listed formulations, therefore, comprise the listed components and any minor materials associated with such components.

I claim:

1. An 10-90% aloe vera liquid composition for inhalation or vaping consisting of aloe vera liquid and at least one antioxidant selected from the group consisting of a carotenoid, glutathione, an alpha lipoic acid, a flavonoid, an oleanoic acid, ascorbyl palmitate, melatonin, a B-Vitamin, an amino acid, an omega-6 fatty acid, and a vitamin E acetate.

2. The composition of claim 1, further comprising a lubricating agent.

3. The composition of claim 1, further comprising at least one lubricating agent chosen from a cellulose derivative, sodium carboxymethyl cellulose, hydroxypropyl methylcellulose, glycerin, polyvinyl alcohol, polyvinylpyrrolidone, povidone, propylene glycol, mineral oil, lactoferrin, and albumin.

4. The composition of claim 1, further comprising at least one additional component chosen from a vehicle, a buffer, an organic carrier, an inorganic carrier, an emulsifier, a wetting agent, an anti-inflammatory agent, a penetration enhancer, a nerve sheath protectant, a nitric oxide synthase inhibitor, and a preservative.

5. The composition of claim 1, further comprising 0.5% zinc sulfate heptahydrate, and 0.010% benzalkonium chloride.

6. The composition of claim 1, further comprising aloe vera liquid 30% (q.s), glycerin 70%, pyridoxine 0.2%, methylcobalamin 0.1%, and tetramethylhydrofolate 0.1%.

7. The composition of claim 1, further comprising aloe vera liquid 70% (q.s), glycerin 30%, theanine 5%, and resveratrol 5%.

8. The composition of claim 1, further comprising aloe vera liquid 40% (q.s), glycerin 60%, gamma aminobutyric acid 10%, and melatonin 2%.

9. The composition of claim 1, further comprising aloe vera liquid 50% (q.s), glycerin 50%, n-acetyl-cysteine 10%, and glutathione 10%.

* * * * *